US00PP24155P2

(12) United States Plant Patent
Eggleton

(10) Patent No.: US PP24,155 P2
(45) Date of Patent: Jan. 7, 2014

(54) SALVIA PLANT NAMED 'EGGBEN003'

(50) Latin Name: *Salvia microphylla×greggii*
Varietal Denomination: EGGBEN003

(76) Inventor: Steven Eggleton, Wonga Park (AU)

( * ) Notice: Subject to any disclaimer, the term of this patent is extended or adjusted under 35 U.S.C. 154(b) by 127 days.

(21) Appl. No.: 13/506,161

(22) Filed: Mar. 30, 2012

(51) Int. Cl.
*A01H 5/00* (2006.01)

(52) U.S. Cl.
USPC ..... Plt./475

(58) Field of Classification Search
USPC ..... Plt./475
See application file for complete search history.

(56) References Cited

U.S. PATENT DOCUMENTS

PP20,929 P2 * 4/2010 Jones ..... Plt./475

* cited by examiner

*Primary Examiner* — Wendy C Haas
(74) *Attorney, Agent, or Firm* — Cassandra Bright

(57) ABSTRACT

A new and distinct *Salvia* cultivar named 'EGGBEN003' is disclosed, characterized by having distinctive lavender flowers, a compact, very well-branched plant habit, and early, flowering. The new variety is a *Salvia*, normally produced as an outdoor garden or container plant.

2 Drawing Sheets

Figure 1:
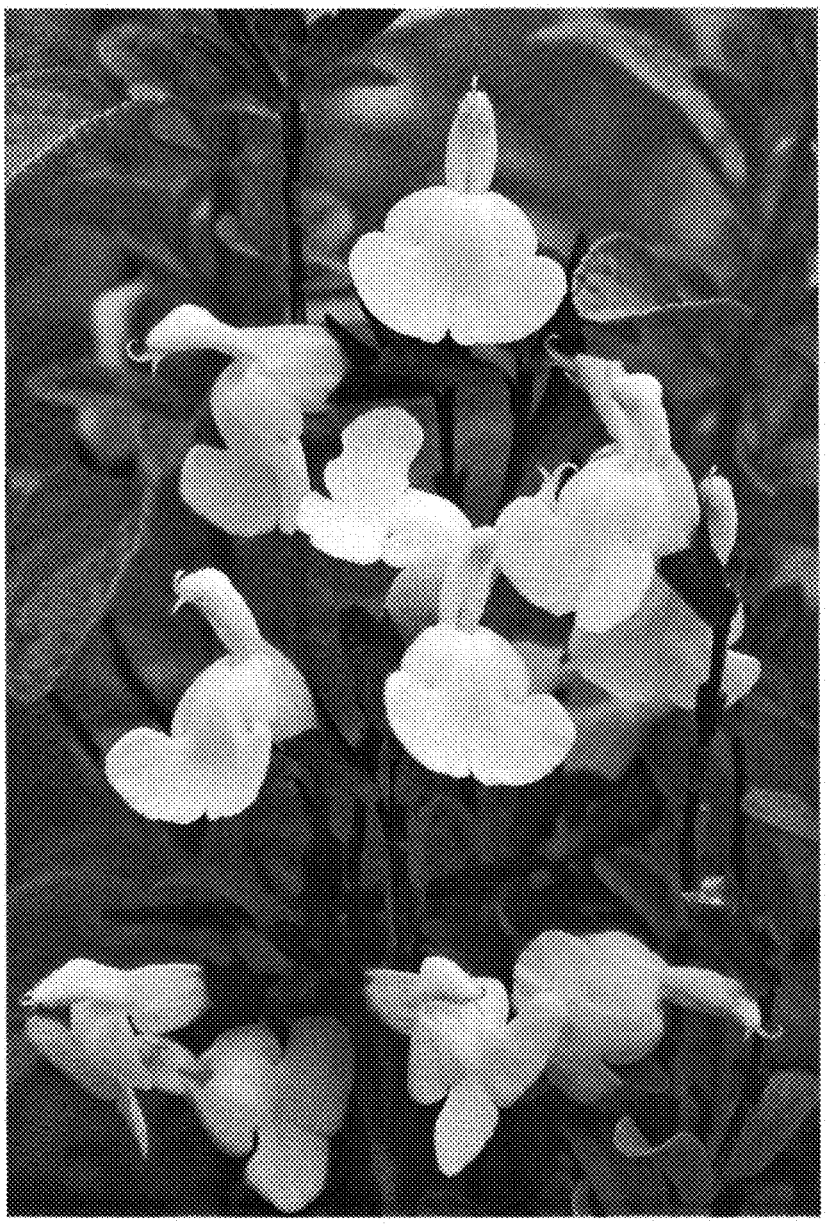

Latin name of the genus and species: *Salvia microphylla× greggii.*

Variety denomination: 'EGGBEN003'.

BACKGROUND OF THE INVENTION

The new *Salvia* cultivar is a product of a planned breeding program conducted by the inventor, Steve Eggleton, in Wonga Park, Victoria, Australia. The objective of the breeding program was to produce new *Salvia* varieties with denser plant habits, strong garden performance, in a range of flower colors. The cross resulting in this new variety was made during April 2006.

The seed parent is the unpatented, *Salvia microphylla* 'Trebah'. The pollen parent is the unpatented, proprietary variety *Salvia greggii* '005'. The new variety was identified as a potentially interesting selection in October 2006, at a research greenhouse in Wonga Park, Australia. Further observations and evaluations were made during 2007.

Asexual reproduction of the new cultivar 'EGGBEN001' by vegetative cuttings was first performed during 2007, at a research greenhouse in Wonga Park, Australia. Subsequent propagation has shown that the unique features of this cultivar are stable and reproduced true to type on successive generations.

SUMMARY OF THE INVENTION

The cultivar 'EGGBEN003' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EGGBEN003' These characteristics in combination distinguish 'EGGBEN003' as a new and distinct *Salvia* cultivar:

1. Bushy plant habit.
2. Creamy white flowers.

3. Dark coloring of calyx
4. Strong, rigid inflorescence.
5. Dense plant habit.

PARENT COMPARISON

Plants of the new cultivar 'EGGBEN003' are similar to plants of the seed parent, *Salvia microphylla* 'Trebah' in most horticultural characteristics, however, plants of the new cultivar 'EGGBEN003' are denser, with a less upright plant habit. Additionally, flowers of the parent do not produce the dark calyx coloration found in the new variety.

Plants of the new cultivar 'EGGBEN003' are similar to plants of the pollen parent, *Salvia greggi* '005' in most horticultural characteristics, however, plants of the new cultivar 'EGGBEN003' produce creamy white flowers whereas the pollen parent produces red flowers.

COMMERCIAL COMPARISON

Plant of the new cultivar are best compared to the commercial variety *Salvia greggii×microphylla* 'CATHEDRAL SKY BLUE', U.S. Plant Pat. No. 20,929. Plants of the new variety are

COMMERCIAL COMPARISON

Plant of the new cultivar are best compared to the commercial variety *Salvia jamensis* 'La Luna', unpatented. Plants of the new variety produce a calyx with significant dark coloration not found on the comparator. Additionally, the varieties differ in leaf shape.

Plant of the new cultivar are best compared to the commercial variety *Salvia jamensis* 'Moonlight Serenade', unpatented. Plants of the new variety produce much glossier foliage than the comparator. Additionally, the new variety has a more spreading, less upright plant habit.

BRIEF DESCRIPTION OF THE PHOTOGRAPHS

The accompanying photograph in FIG. 1 illustrates in full color a typical flower of 'EGGBEN001'.

Figure 2:
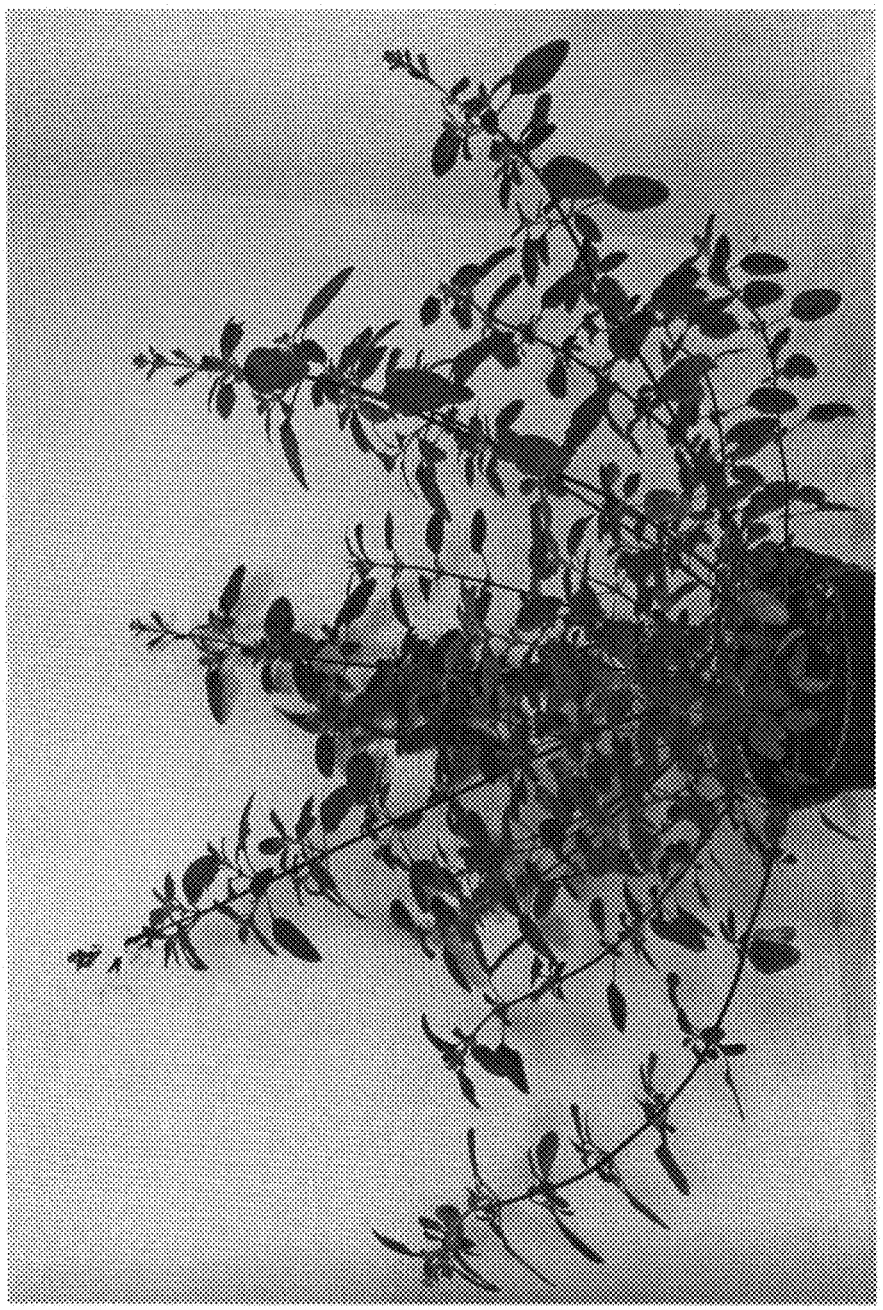

FIG. 2 illustrates in full color a typical plant of 'EGGBEN001' grown in a greenhouse, in Watsonville, Calif., in a commercial 8 inch container. Age of the plant photographed is approximately 20 weeks from an unrooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 Edition, except where general terms of ordinary dictionary significance are used. The following observations and measurements describe 'EGGBEN003' plants grown in a greenhouse in Lompoc, Calif. The growing temperature ranged from 10° C. to 28° C. The greenhouse is un-shaded, giving bright, normal sunlight conditions. Measurements and numerical values represent averages of typical plant types.

Time to Produce A Rooted Cutting: About 21 days at 25° C.

PLANT

Growth habit: Upright annual.

Pot size of plant described: 8 inch pot.

Height: Approximately 30 cm to top of foliage. Approximately 40 cm to top of flowering plane. Measured from soil level of pot.

Plant spread: Approximately 60 cm.

Growth rate: Rapid.

Branching characteristics: Free-branching, Approximately 8 primary branches.

Length of primary lateral branches: Approximately 35 cm.

Diameter of lateral branches: Approximately 0.45 cm

Quantity of lateral branches: About 18 to 24.

Stem:

*Color*.—Near RHS Greyed-Purple N187B.

*Pubescence*.—Minute pubescence.

Internode length: Approximately 3.0 to 4.0 cm.

Age of plant described: Approximately 20 weeks from an unrooted cutting.

FOLIAGE

Leaf:

*Arrangement*.—Opposite.

*Quantity*.—Approximately 16 fully expanded per main branch.

*Average length*.—Approximately 5.5 cm., including petiole.

*Average width*.—Approximately 2.1 cm.

*Shape of blade*.—Obovate.

*Apex*.—Obtuse.

*Base*.—Obtuse to nearly truncate.

*Attachment*.—Stalked.

*Margin*.—Crenate.

*Texture of top surface*.—Matte, minute, coarse pubescence.

*Texture of bottom surface*.—Matte, minute, coarse pubescence.

*Color*.—Young foliage upper side: Near RHS Green 137A. Young foliage under side: Near RHS Green 137C. Mature foliage upper side: Near RHS Green 137A. Mature foliage under side: Near RHS Green 137C.

*Venation*.—Type: Pinnate. Venation color upper side: Near RHS Yellow-Green 144A. Venation color under side: Near RHS Green 143C.

*Petiole*.—Average Length: Approximately 1.7 cm. Diameter: Approximately 0.15 cm. Color: Near Green 143C.

FLOWER

Natural flowering season: Flowering from early Spring through late Summer.

Inflorescence type and habit: Flowers arranged in verticillasters on spikes.

Flower longevity on plant: Individual flowers last approximately 1 week on the plant. Each spike lasts approximately 7 weeks with flowers.

Quantity of flowers: About 8 buds and 6 fully opened flowers per spike, at one time. Mature plants have approximately 14 to 18 spikes.

Spike size:

*Diameter*.—Approximately 6.0 cm.

*Height*.—Approximately 6.5 cm.

Individual flowers:

*Size*.—Diameter: Approximately 2.1 cm. Length: Approximately 2.8 cm.

*Persistence*.—Non-persistent.

*Fragrance*.—Moderate, typical Salvia scent.

Corolla:

*Petal arrangement*.—The corolla is sympetalous and typically bilabiate with 2 small, highly fused lobes forming an upper lip and 3 larger highly fused lobes forming a lower lip.

*Margin*.—Nearly entire, slightly scalloped

*Tip shape*.—Upper lip tip retuse, lower lip tip rounded with scallops.

*Length*.—Upper lip Approximately 1.0 cm, lower lip Approximately 1.5 cm. Tube length Approximately 2.0 cm.

*Width*.—Upper lip Approximately 0.4 cm, lower lip Approximately 2.0 cm. Tube width Approximately 0.9 cm.

*Texture*.—Upper lip: Some feathery pubescence on exterior surface. Interior surface glabrous. Lower lip: Glabrous all surfaces.

Color:

*Upper lip*.—When opening: Inner surface: Near RHS Yellow 11D. Outer surface: Near RHS Yellow 11D, very slight flush Red 53C. Fully opened: Inner surface: Near RHS Yellow-White 158D. Outer surface: Near RHS Yellow-White 158D, faint flush Red 54B. Fading: Inner surface: Near RHS Yellow-White 158D. Outer surface: Near RHS Yellow-White 158D, faint flush Red 54B.

Color:

*Lower lip*.—When opening: Inner surface: Near RHS Yellow 10D. Outer surface: Near RHS Yellow 10D. Fully opened: Inner surface: Near RHS Yellow-White 158B. Outer surface: Near RHS Yellow-White 158C. Fading: Inner surface: Near RHS Yellow-White 158D. Outer surface: Near RHS Yellow-White 158D.

Color:

*Tube*.—When opening: Inner surface: Near RHS Yellow-White 158B, faint flush near Red 52B. Outer surface: Near RHS Yellow-White 158B, faint flush near Red 52B. Fully opened: Inner surface: Near RHS Yellow-White 158D. Outer surface: Near RHS Yellow-White 158B. Fading: Inner surface: Near RHS Yellow-White 158D. Outer surface: Near RHS Yellow-White 158D.

Bud:

*Shape*.—Ovoid.

*Length*.—Approximately 1.7 cm.

*Diameter*.—Approximately 0.7 cm.

*Color*.—Near RHS Yellow 11C with strong flush near Red 53D.

Calyx:

*Length*.—Approximately 1.5 cm.

*Diameter*.—Approximately 1.0 cm.

*Shape*.—Tubular.

*Sepals*.—Shape: Quantity per flower: 3, fused to form a tube. Unfused Apex: Length: Approximately 0.5 cm. Width: Approximately 0.6 cm. Margin: Entire. Apex: Acute. Texture: Pubescent. Color: Immature: Near RHS Yellow-Green 144A. Mature: Near RHS Greyed-Purple N186B.

Peduncle:

*Length*.—Average 2.5 cm.

*Diameter*.—0.35 cm.

*Color*.—Near RHS Yellow-Green 144B, occasional thin stripe near Greyed-Purple N186D.

*Orientation*.—Upright, straight.

*Strength*.—Strong.

*Texture*.—Pubescent.

Pedicels:

*Length*.—Average 0.4 cm.

*Diameter*.—0.15 cm.

*Color*.—Near RHS Greyed-Purple N186B.

*Orientation*.—Straight, approximately 45 degree angle from attachment.

*Strength*.—Flexible.

*Texture*.—Pubescent.

REPRODUCTIVE ORGANS

Stamens:

*Number*.—2.

*Filament length*.—Approximately 1.5, approximately 1.0 cm of length fused to petal.

*Filament color*.—Near RHS White 155C.

Anthers:

*Shape*.—Very narrowly elliptic.

*Length*.—Approximately 3 mm.

*Color*.—Near RHS Yellow-White 158A.

*Pollen*.—Scant, colored near Greyed-Orange 168D.

Pistil:

*Number*.—1.

*Length*.—Approximately 2.8 cm.

*Style*.—Length: Approximately 2.5 cm. Color: Near RHS White N155A.

*Stigma*.—Shape: Linear, curled. Color: Near RHS White N155A. Ovary color: Near RHS Yellow-Green 154A.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'EGGBEN003' as herein illustrated and described.

* * * * *